United States Patent [19]

David et al.

[11] Patent Number: 4,488,114

[45] Date of Patent: Dec. 11, 1984

[54] DEVICE FOR NON-DESTRUCTIVE TESTING BY EDDY CURRENTS COMPRISING AIR-GAP CORRECTION MEANS

[75] Inventors: Bernard David, Gif-Sur-Yvette; Michel Pigeon, Bures Sur Yvette, both of France

[73] Assignee: Commissariat a l'Energie Atomique, Paris, France

[21] Appl. No.: 360,901

[22] Filed: Mar. 23, 1982

[30] Foreign Application Priority Data

Mar. 23, 1981 [FR] France ................................. 81 05753

[51] Int. Cl.³ ..................... G01N 27/72; G01N 27/82; G01R 33/12
[52] U.S. Cl. .................................... 324/225; 324/241; 324/242; 324/243
[58] Field of Search ......... 324/225, 226, 227, 239–243

[56] References Cited

U.S. PATENT DOCUMENTS 4,079,312 3/1978 Osborn et al. ...................... 324/242
4,109,201 8/1978 Pigeon et al. ...................... 324/227

Primary Examiner—Gerard R. Strecker
Assistant Examiner—Walter E. Snow
Attorney, Agent, or Firm—James E. Nilles

[57] ABSTRACT

Process and device for non-destructive testing or inspection by eddy currents with correction of the air gap effects. A differential measurement and an absolute measurement are performed and the result of the former is divided by that of the latter, which supplies a signal with respect to which the effects of the air gap separating the probe from the member to be inspected are corrected. Application to the inspection and testing of metal members.

9 Claims, 11 Drawing Figures

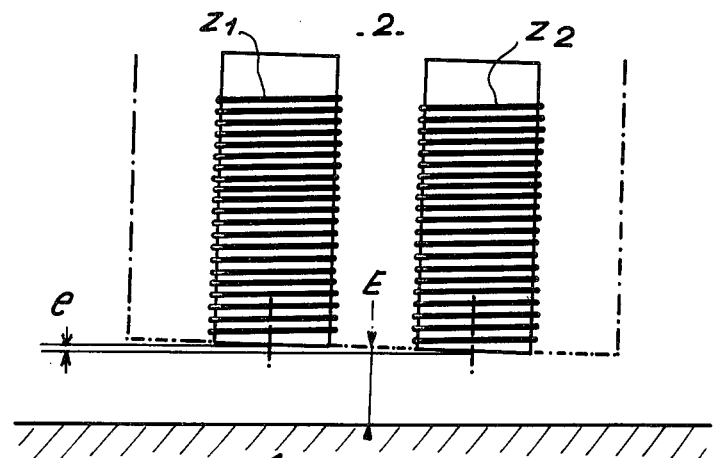
PRIOR ART  FIG.1a
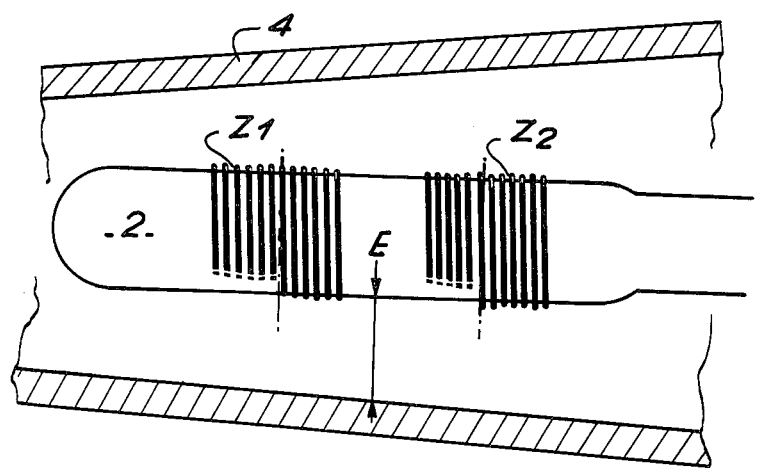
FIG.1b  PRIOR ART

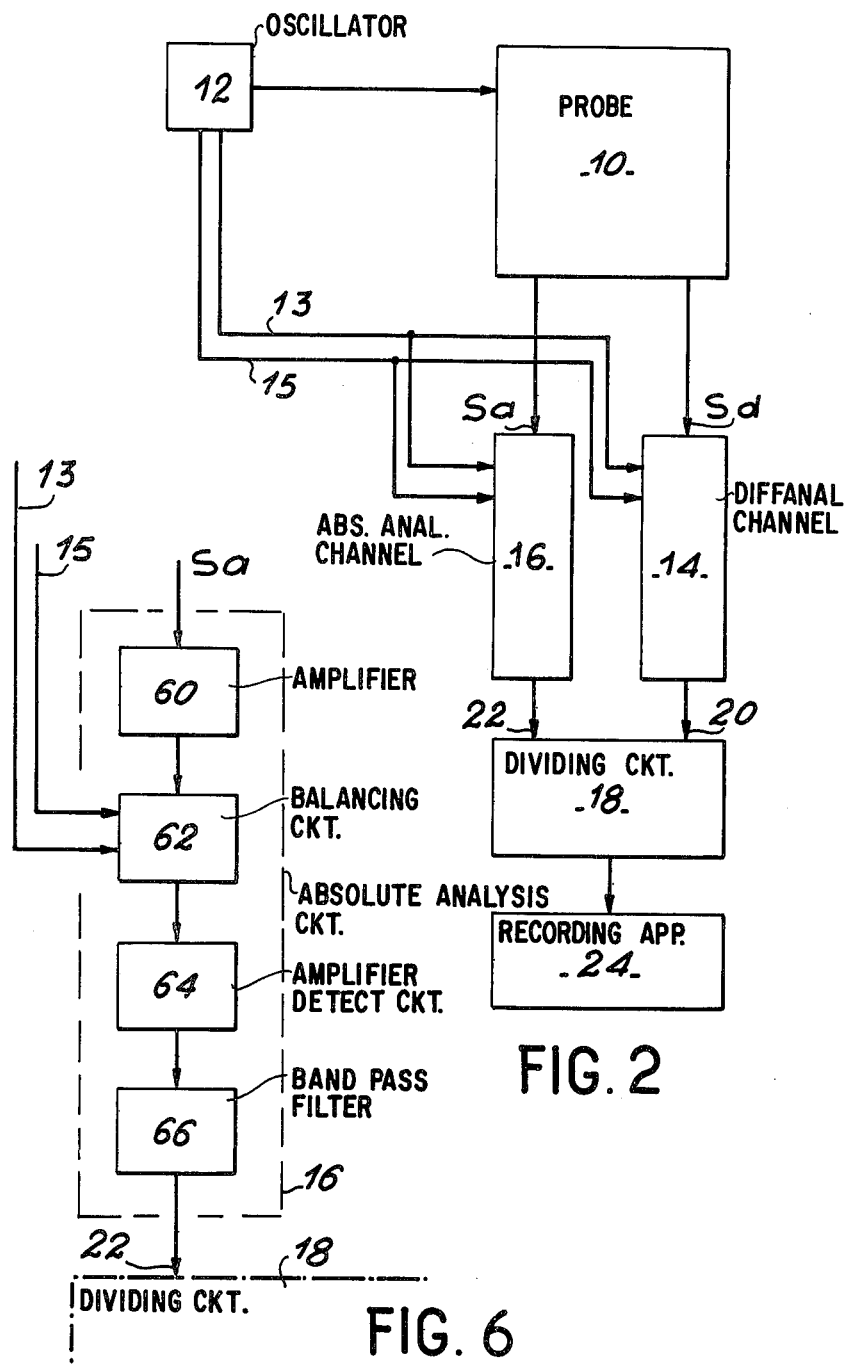

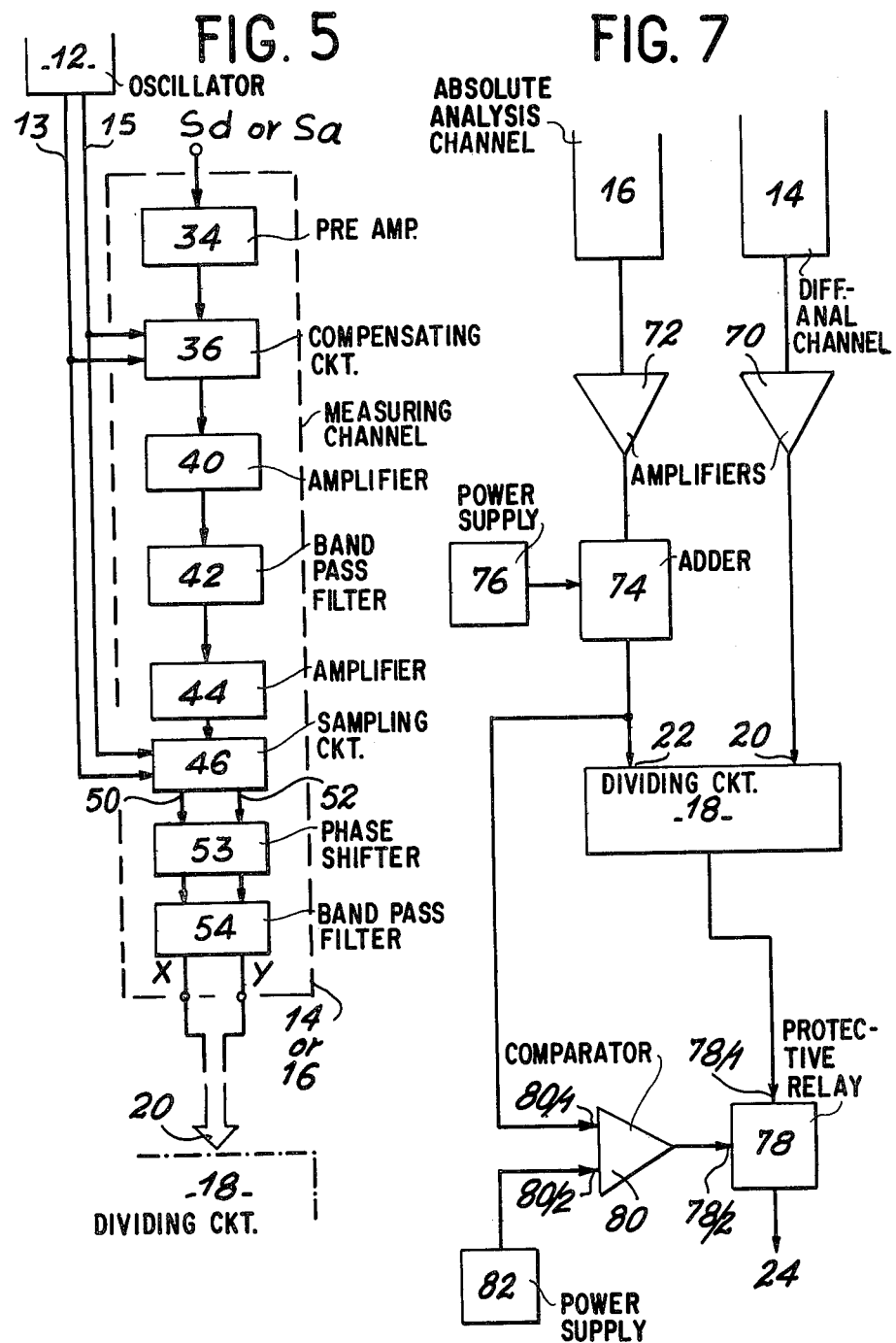

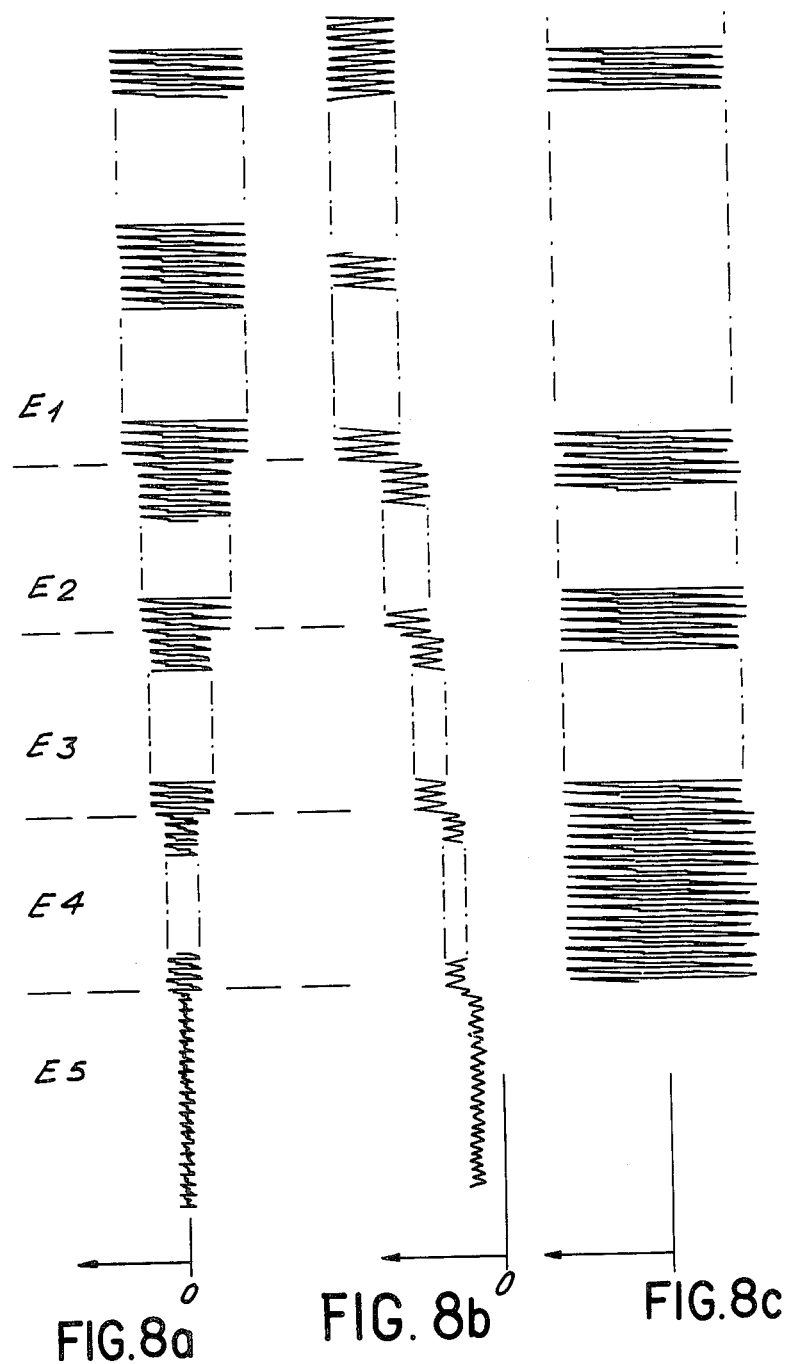

DEVICE FOR NON-DESTRUCTIVE TESTING BY EDDY CURRENTS COMPRISING AIR-GAP CORRECTION MEANS

BACKGROUND OF THE INVENTION

The present invention relates to a process for the non-destructive testing by eddy currents with a correction of the air gap effects and an apparatus for performing this process. It is used in the testing and inspection of metal parts, particularly tubes, plates, etc.

Inspection by eddy currents consists of studying the variations of the currents induced in a metal part by the magnetic field of a coil, traversed by an alternating exciting current. In turn these currents produce a magnetic field, which opposes the induction field, thereby modifying the impedance of the exciting coil. This coil is located in a sensor or probe moved along the member to be inspected or tested. Any fault or defect in the latter (change of size, variation in the conductivity, cracks, etc.) modifies the path or intensity of the eddy currents and correlatively the impedance of the coil.

The probe is generally constituted by two adjacent coils, supplied in opposition and placed in the two adjacent branches of a measuring bridge. The passage of a fault in the field of the probe unbalances the bridge twice, firstly in one direction and then in the other. The voltage supplied by the probe is analyzed and displayed on the screen of a cathode tube by its resistive component X (or real component), which is the component in phase with the exciting current, and its reactive component Y (or imaginary component) which is the component in phase quadrature with the exciting current. The complex voltage supplied by the probe is consequently represented by a point of coordinates X, Y. When a fault passes in the field of the probe, the representative point plots a curve having two lobes in the form of a figure of eight. Each fault can then be identified on the basis of the phase of the lobes (slope relative to the reference axis) and the amplitude thereof.

To obtain a good level of accuracy in the location of faults, it is necessary to use very small probes. However, the problem of air gap variations is quickly encountered. To provide a better understanding of this problem, which forms the basis for the invention, the question will firstly be defined in conjunction with FIGS. 1a and 1b.

FIGS. 1a and 1b illustrates two types of probe or sensor commonly used in the field of inspection and testing by eddy currents. These probes essentially comprise a body 2 provided with two windings $Z_1$ and $Z_2$. They travel in front of or in the member 4 to be inspected. The air gap is formed by the space separating the probe from the member to be inspected and is designated E in FIGS. 1a and 1b.

It is in fact an average air gap, because the probe is not necessarily strictly parallel to the member to be inspected. Therefore, there can be a "differential" air gap, designated e, which represents the difference between the air gaps of each winding. However, no account will be taken hereinafter of the differential air gap, whose effects can be corrected by filtering. The essence of the invention relates to the correction of the air gap E, being common to both windings.

If this air gap was constant throughout the measurement, it would only lead to an attenuation of the signal, which could be compensated by amplifying the detected signals. In actual fact, due to the movement of the probe along the member, said air gap varies constantly. Thus, there is a permanent and unpredictable modification of the measuring signal. Thus, the intensity of this signal not only depends on the detected fault, but also on the distance between the probe and the member to be inspected or tested. This is due to the fact that the intensity of the currents induced in an area of the member to be tested is dependent on the magnetic induction created in this area and that the latter decreases when the distance from the field windings increases.

In the same way, the action of the eddy currents on the windings is also dependent on this distance.

If it is wished to correct the effects of air gap variations on the result of the measurement, it is necessary to record the value of the air gap at all times. Even if such a process could be performed, it would be extremely difficult, because it would require not only air gap measuring means, but also correction circuits based on a law which, by its very nature, is very complex.

BRIEF SUMMARY OF THE INVENTION

The problem of the present invention is to obviate these difficulties by providing a correction process and apparatus of maximum simplicity.

To this end, the invention proposes correcting a differential measurement on the basis of the result obtained by an absolute measurement. This correction is simply obtained by dividing the result of the differential measurement by that of the absolute measurement. This leads in a surprising manner to a result, which is substantially independent of the air gap.

The simplicity of such a process is obvious, because it is based solely on a processing of signals supplied by the probe, without requiring the explicit determination of the air gap or the processing of a correction signal which is a function of the air gap. In other words, the Applicant has found that the absolute signal synthesizes to a certain extent the effects of the air gap and that this signal can in itself constitute a correction means.

The process of the invention implies that it is simultaneously possible to perform a differential measurement and an absolute measurement with the same probe. If the two windings of a probe are sensitive to the faults or defects of the part to be tested, the bridge makes it possible to perform a differential measurement. If only one of these windings is sensitive to the faults of the member to be tested, the bridge makes it possible to perform an absolute measurement. Some bridges are double, in that they comprise both a differential measuring bridge and an absolute measuring bridge, said two bridges having in common one of the windings sensitive to the faults of the member to be inspected or tested. A bridge of the latter type is well suited to the performance of the invention. However, it would also be possible to use a probe having a differential measuring bridge with two windings sensitive to the member to be tested and a special winding sensitive to the member to be tested, the latter winding supplying the absolute signal.

More specifically the present invention relates to a process for non-destructive testing by eddy currents with correction of the air gap effects in which a probe is used, which comprises two windings supplied in opposition by an exciting current having a given frequency, said windings being sensitive to the member to be tested and belonging to a balanced bridge and in which a differential measurement is performed by sampling an unbalanced voltage of the bridge and analyzing this voltage at the said frequency, wherein additionally an absolute measurement is performed by sampling a voltage on the winding sensitive to the member to be tested and by analyzing this voltage at the said frequency, and wherein the result of the differential measurement is divided by that of the absolute measurement.

The winding used for the absolute measurement is advantageously one of the two windings used for the differential measurement.

The invention also relates to an apparatus for the non-destructive testing by eddy currents permitting a correction of air gap effects, for performing the process defined hereinbefore. This device comprises a probe having at least two windings connected in opposition by an exciting current having a given frequency, said windings belonging to a differential measuring bridge and are sensitive to the member to be tested, said device also comprising a differential analysis channel supplied by the differential measuring bridge, wherein the probe used also comprises an absolute measuring winding sensitive to the member to be tested and wherein the device also comprises an absolute analysis channel supplied by the absolute measuring winding and a dividing circuit with two inputs, the dividend input being connected to the output of the differential measuring channel, whilst the divisor input is connected to the output of the absolute measuring channel and to an output which supplies a differential measuring signal which has been corrected with respect to the air gap effects.

BRIEF DESCRIPTION OF THE DRAWINGS

The invention is described in greater detail hereinafter relative to non-limitive embodiments and with reference to the attached drawings, which, following on to the already described FIGS. 1a and 1b show:

FIG. 2 a block diagram of a device according to the invention.

FIG. 5 a diagram of a differential and/or absolute measuring channel.

FIG. 6 a diagram of a simplified embodiment of an absolute measuring channel.

FIG. 7 a few supplementary circuits facilitating the realization of the device.

FIGS. 8a, 8b and 8c an experimental diagram respectively showing the differential and absolute measuring signals, as well as a differential measuring signal corrected according to the invention.

DETAILED DESCRIPTION OF THE PREFERRED EMBODIMENTS

Figure 3:
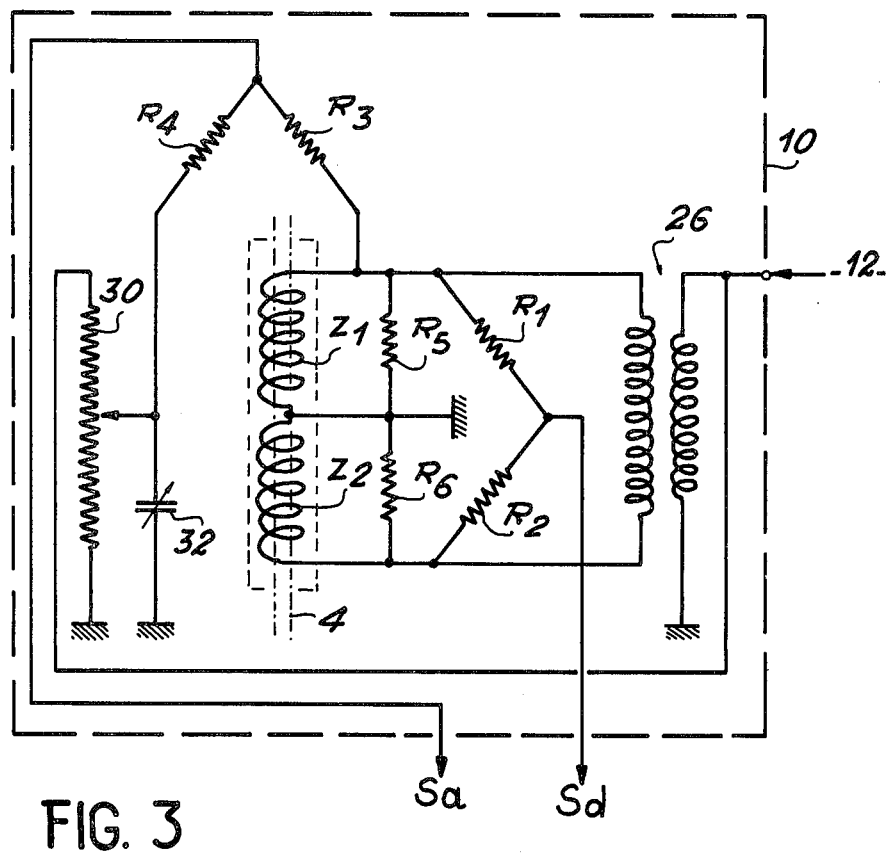
FIG. 3 a double differential and absolute measuring bridge usable in the invention.

The device of FIG. 2 comprises a measuring probe or sensor 10, e.g. of the type having a double measuring bridge with two outputs, namely one differential output Sd and the other absolute output Sa; an oscillator 12 for supplying the probe at a given frequency; a differential analysis channel 14; an absolute analysis channel 16; a dividing circuit 18 with two inputs, the dividend signal, in the present case the differential measuring signal being supplied to one input 20 and the divisor signal, in this case the absolute measuring signal being applied to the other input 22; and a member 24 for the recording or display of the signal supplied by dividing circuit 18.

The operation of the device can be gathered from what has been stated hereinbefore. Probe 10 supplies two signals, one coming from a differential bridge and the other from an absolute bridge. Channels 14 and 16 analyze the signals. Thus, they measure the component of these signals in phase with the exciting current of the probe and the component in phase quadrature with the same current. To this end, channels 14 and 16 receive currents respectively in phase and in phase quadrature with the exciting current applied to probe 10 from oscillator 12 via two connections 13 and 15. The result of the differential measurement is then divided by that of the absolute measurement in dividing circuit 18. The thus corrected differential measurement is then substantially independent of the air gap separating the probe from the member to be tested or inspected.

FIGS. 3 to 6 illustrate a number of embodiments of means which can be used for forming probe 10 and channels 14 and 16. These means are known per se if they are considered in isolation.

FIG. 3 shows a double bridge comprising both an absolute measuring bridge and a differential measuring bridge. The differential measuring bridge comprises two resistors $R_1$ and $R_2$ and two windings $Z_1$ and $Z_2$ traversed by the member 4 to be tested.

According to an improved embodiment supplementary resistors $R_5$ and $R_6$ can be connected in parallel to the two windings $Z_1$ and $Z_2$. The output enabling the performance of the differential measurement is designated Sd. Power is supplied to the bridge via the secondary of a transformer 26, whose primary receives an exciting current from oscillator 12.

The part corresponding to the absolute measuring bridge is constituted by two resistors $R_3$ and $R_4$, by winding $Z_1$ (and its associated resistor $R_5$) and by a circuit making it possible to compensate the exciting voltage. This circuit comprises a potentiometer 30, to which is applied the supply voltage from the primary of transformer 26 and a variable capacitor 32. The recording of the absolute signal Sa takes place between resistors $R_3$ and $R_4$. The regulation of potentiometer 30 and capacitor 32 makes it possible to obtain the balancing of the absolute bridge in order that the voltage appearing at the absolute output connection Sa is free from the exciting signal.

Figure 4:
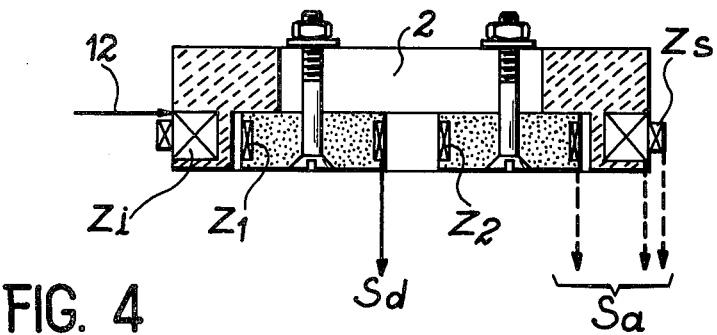
FIG. 4 a special embodiment of a probe usable in the invention.

Naturally other types of probe can be used. For example it is possible to add to a differential bridge, a special supplementary winding for supplying the absolute signal required for correction. It is also possible to use a probe having a field winding and two reception windings, as illustrated in FIG. 4. In FIG. 4 a field winding Zi is supplied by power supply 12, two reception windings $Z_1$ and $Z_2$ connected in opposition being located within winding Zi. This probe has no magnetic cores. The different windings are wound on to resin mandrels able to withstand high temperatures (250° C.). The differential signal Sd is taken between windings $Z_1$ and $Z_2$ and the absolute signal Sa is sampled either at the terminals of field winding Zi, or at the terminals of one of the reception windings $Z_1$ or $Z_2$, or at the terminals of a supplementary winding Zs wound around the field winding.

The circuit of FIG. 5 represents either a measuring channel 14 for the differential signal appearing at the output Sd of the probe, or a measuring channel 16 from the absolute signal appearing at output Sa, although the last-mentioned channel can be simplified in the manner to be described relative to FIG. 6.

In FIG. 5 the circuit shown firstly comprises a preamplifier circuit 34, e.g. with a gain of 30 decibels for giving the measuring signal an adequate level to enable it to carry out the balancing operations. The latter consist of compensating the unbalance of the construction of the probe and are performed in a circuit 36. The latter is connected to oscillator 12 by connections 13 and 15, which carry signals respectively in phase and in phase quadrature with the exciting current of the probe. After balancing the measuring signal is amplified in an amplifier circuit 40, e.g. of a gain 60 decibels, said amplification being such that the signal is not saturated. The signal supplied by amplifier circuit 40 is then filtered by a band-pass filter 42, centered on the exciting frequency. The filter advantageously has sharp flanks, e.g. 24 decibles per octave. The filtered signal is applied to an amplifier circuit 44 and is then analyzed by a memory sampling circuit 46 or by any other demodulation system (multiplier, synchronous detector, etc.). This circuit receives via connections 13 and 15, two reference signals in phase and in phase quadrature with the exciting current of the probe. This memory sampler supplies on two output connections 50, 52 the part in phase X and the part in phase quadrature Y with the exciting current. This sampler may optionally be followed by a phase shifter 53 permitting the rotation of the plane XY obtained by an angle between 0° and 360°. The phase shifter can itself be followed by a bandpass filter 54, which makes it possible to eliminate the residual background noise due to the sampling operation or eliminate the effect of the differential air gap.

Thus, the represented channel difinitively supplies the resistive part X and reactive part Y of the differential or absolute signal. These signals X and Y are are d.c. voltages, which are slowly variable with the displacement of the probe.

It is obvious that this circuit is only given for illustrative purposes and that the invention also permits the use of any means making it possible to determine the resistive and reactive parts of the signal.

If a channel like that of FIG. 5 is used as the analysis circuit for the absolute signal, the two components X and Y of the signal are available and for performing the correction it is possible to use either one of these components, or both of them, or the modulus $\sqrt{X^2+Y^2}$.

Component X is particularly useful because it decreases when the air gap increases and therfore forms an interesting dividing parameter. Moreover, a phase rotation obtained by phase shifter 53 makes it possible to obtain a maximum sensitivity for component X.

However, for processing the absolute signal, it is also possible to use a simplified channel, like that shown in FIG. 6. This channel does not supply components X and Y separately and instead only supplies the modulus of the signal. The represented channel comprises an amplifier 60, a balancing circuit 62, an amplitude detection circuit 64 and a band-pass filter 66.

However, a precaution must be taken when using the modulus extracted from a simplified channel. Thus, if the balancing operation was performed when the sensor or probe was closed to the member, the modulus of the measuring signal would have a high value with a large air gap and a low value with a small air gap. Therefore such a signal could not form a correct divisor, because it does not vary in the proper way. Thus, the balancing operation is performed when the probe is remote from the considered surface. In this case, on the basis of the components of the exciting signal carried by connections 13 and 15, components such that the modulus of the balanced signal is zero are opposed to the components of the absolute measuring signal. Then, when the probe moves towards the member to be inspected, the module supplied by the circuit 64 increases and this module can then form a divisor.

In the manner illustrated in FIG. 7, a certain number of auxiliary circuits can be used to facilitate the performance of the process according to the invention. The signal supplied by the differential channel can be amplified by a circuit 70, e.g. having a gain of 20 dB. The absolute signal can firstly pass through a unity gain amplifier 72, which matches the impedances and can then undergo a zero regulation by means of an adder 74 supplied by a regulatable power supply 76. As the probe is remote from any metal part, power supplies 76 is regulated until, at the output of circuit 74, a zero signal constituting the zero point is obtained. It is also necessry to ensure that the absolute signal used for dividing the differential signal does not become zero, in which case the corrected signal supplied by dividing circuit 18 would become infinite. Thus, it is possible to arrange at the output of dividing circuit 18 a protective relay 78, whereof one signal input 78/1 receives the corrected differential signal and a control input 78/2 receives a voltage supplied by a comparator 80. The latter has two inputs 80/1 and 80/2, the former receiving the signal supplied by the adder 74 and the second receiving a signal supplied by a regulatable power supply 82. When the absolute signal applied to the input 22 of the dividing circuit drops to a value below the threshold fixed by the power supply 82, comparator 80 supplies a voltage which is able to open the relay 78. This prevents the saturation of the following recording device 24. Thus, recording is not possible when the air gap exceeds a certain value and the signal-to-noise ratio becomes too low. In general the threshold is set between one third and half the absolute signal corresponding to the probe-member contact (zero or quasi-zero air gap).

The curves of FIG. 8 demonstrate an example of the results obtained as a result of the invention. The measurements are performed for increasing air gap values $E_1, E_2 \ldots E_5$, by rotating a metal member in the vicinity of a probe. Diagram (a), to the left, shows an uncorrected differential signal. Diagram (b), in the centre, shows the corresponding absolute signal. These two diagrams show that the sensitivity of the measurement decreases when the air gap increases. Diagram (c), to the right, shows the differential signal corrected in accordance with the invention, i.e. obtained by dividing differential signal (a) by absolute signal (b). It can be seen that the thus corrected signal has a substantially constant intensity, no matter what the value of the air gap between $E_1$ and $E_4$. For value $E_5$, the corrected signal is interrupted, because the absolute signal becomes too low and the relay 78 of FIG. 7 opens indicating that the quality of the measurement is no longer satisfactory.

The invention described hereinbefore can be used on any type of surface, either in high frequency (1 kHz to 1 MHz) e.g. for the detection of longitudinal or transverse faults inside or outside tubes or cylindrical or conical bores, or at low frequency (a few Hz to a few kHz) e.g. for the testing of joints or welds, as well as for the detection of defects beneath a coating.

What is claimed is:

1. A device for non-destructive testing by eddy currents permitting a correction of air gap effects, comprising a probe having at least two windings connected in opposition and supplied by an exciting current having a given frequency, said windings belonging to a differential measuring bridge and being sensitive to adjacent areas of the member to be tested, said device also comprising a differential analysis channel supplied by the differential measuring bridge, wherein the probe used also comprises an absolute measuring winding sensitive to the member to be tested and wherein the device also comprises an absolute analysis channel supplied by the absolute measuring winding and a dividing circuit with a dividend input and a divisor input, said dividend input being connected to the output of the differential measuring channel, whilst said devisor input is connected to the output of the absolute measuring channel, said dividing circuit having an output which supplies a measuring signal which has been corrected with respect to the air gap effects.

2. A device according to claim 1 wherein the absolute measuring winding comprises one of the windings of the differential measuring bridge.

3. A device according to claim 1, wherein the absolute measuring winding comprises a supplementary winding.

4. A device according to claim 1, wherein the probe comprises a field winding and two reception windings located within the field winding and connected in opposition, the absolute measuring winding being constituted either by one of said field winding and reception windings.

5. A device according to claim 1, wherein it comprises, inserted between the output of the absolute measuring channel and the divisor input of the dividing circuit, a zero regulating circuit controlled by a regulatable power supply.

6. A device according to claim 5, wherein it also comprises a comparator with two inputs, the first being connected to the output of the zero regulation circuit and the second to a regulatable power supply, and a protective relay having one signal input connected to the output of the dividing circuit and a control input connected to the output of the comparator, said protective relay being open when the voltage applied to the first input of the comparator is below the voltage applied to the second input.

7. A device according to claim 1, wherein the differential analysis channel and the absolute analysis channel comprise in each case circuits which are able to measure the two components in phase and in phase quadrature with respect to the exciting current.

8. A device according to claim 7, wherein the circuits supply component X in phase and comprise a phase shifter able to increase component X.

9. A device according to claim 1, wherein the differential analysis channel comprises circuits able to measure the two components in phase and in phase quadrature with respect to the exciting current, and wherein the absolute analysis channel comprises an amplifier, a balancing circuit, an amplitude detector and a filter, balancing being performed when the probe is remote from the member to be inspected or tested.

* * * * *